(12) United States Patent
Ooshima et al.

(10) Patent No.: US 6,190,309 B1
(45) Date of Patent: Feb. 20, 2001

(54) VIDEO SCOPE AND PORTABLE ACCOMMODATION CASE THEREFOR

(75) Inventors: Kiyoko Ooshima, Shijonawate; Hiroshi Atsuta, Katano; Shinji Uchida, Neyagawa; Hiroyuki Yamakita, Osaka, all of (JP)

(73) Assignee: Matsushita Electric Industrial Co., Ltd., Osaka (JP)

( * ) Notice: Under 35 U.S.C. 154(b), the term of this patent shall be extended for 0 days.

(21) Appl. No.: 09/188,795

(22) Filed: Nov. 9, 1998

(30) Foreign Application Priority Data

Nov. 7, 1997 (JP) .................................................. 9-305688
Jun. 19, 1998 (JP) ................................................ 10-173663

(51) Int. Cl.⁷ ...................................................... A61B 1/06
(52) U.S. Cl. .......................... 600/179; 600/129; 600/170; 600/177; 600/118
(58) Field of Search ..................................... 600/109, 129, 600/130, 131, 160, 170, 171, 176, 177, 178, 179, 117, 182; 433/29–31; 348/65, 66, 68, 340

(56) References Cited

U.S. PATENT DOCUMENTS

| | | | |
|---|---|---|---|
| 4,114,176 | * 9/1978 | Kawasaki et al. | 354/289 |
| 4,266,534 | * 5/1981 | Ogawa | 600/177 |
| 4,832,003 | * 5/1989 | Yabe | 600/130 |
| 4,868,644 | * 9/1989 | Yabe et al. | 600/130 |
| 4,895,138 | * 1/1990 | Yabe | 600/179 |
| 5,339,446 | * 8/1994 | Yamasaki et al. | 395/750 |
| 5,737,013 | * 4/1998 | Williams et al. | 348/66 |
| 5,745,165 | 4/1998 | Atsuta et al. . | |
| 5,908,294 | * 6/1999 | Schick et al. | 600/179 |
| 5,980,454 | * 11/1999 | Broome | 600/177 |

FOREIGN PATENT DOCUMENTS 62-246347  10/1987 (JP) .
4-176436   6/1992 (JP) .
8-332170  12/1996 (JP) .

* cited by examiner

Primary Examiner—John P. Leubecker
(74) Attorney, Agent, or Firm—Ratner & Prestia (57) ABSTRACT

A video scope has an entry section which can advance into an object; and a grip section which is disposed at the back of the entry section and to be held by an operator, wherein a light reflecting body, an objective lens, a solid-state image pickup device, a light source, a window of incidence for image pickup rays and illumination windows located in the vicinities of the window of incidence are disposed in the entry section, and wherein at least a power source is disposed in the grip section for driving the light source. A portable accommodation case has an accommodation space for accommodating the video scope; and a lid which has a thin display attached thereto, and can rotate freely and stop at an optional position, wherein the thin display is capable of displaying an image which is picked up by the video scope.

18 Claims, 12 Drawing Sheets

(A-A line)

VIDEO SCOPE AND PORTABLE ACCOMMODATION CASE THEREFOR

BACKGROUND OF THE INVENTION

1. Field of the Invention

The present invention relates to a video scope which comprises a solid-state image pickup device such as a CCD.

2. Related art of the Invention

In the recent years, video scopes which utilize CCDs are used in fields of dental surgery and oral surgery for diagnosing affected parts in oral cavities. Such video scopes are classified into two types: one which transmits an illumination rays beam through optical fibers and leads an image of an object to be observed through transfer means such as a lens to a solid-state image pickup device disposed outside an oral cavity like a video scope disclosed by Japanese Patent Application Laid-Open No. 4-176436 and the other type which leads an image of an object to be observed through image fibers to a solid-state image pickup device disposed outside an oral cavity like a video scope disclosed by Japanese Patent Application Laid-Open No. 62-246347.

According to a conventional art disclosed by Japanese Patent Application Laid-Open No. 4-176436, optical fibers used in a light leading path for illumination require disposing lenses and prisms to condense rays onto a section of incidence and project rays to a projector window, and must be disposed in complicated forms so that they are accommodated in a video scope. However, optical fibers which are apt to be easily broken when bent steeply can hardly be stretched to a tip of a video scope and this conventional art hardly allows a number of required parts to be reduced.

Further, this conventional art is configured to connect an electric cable from an external camera circuit to a grip section of a video scope body and connect a optical fiber cable from an external light source box to the grip section, thereby making the video scope equipped with two cables, heavy and low in operability thereof. Further, there is available an electric cable which has built-in optical fibers and is formed as a single cord. When such a cord which is thick and long is connected to a grip section of a video scope body, however, it degrades operability of a video scope or makes it rather inconvenient for handling like the plurality of cables.

Furthermore, a conventional art disclosed by Japanese Patent Application Laid-Open No. 62-246347 or No. 4-176436 is configured to dispose an image pickup device not in a tip to be located in the vicinity of an oral cavity but in a rear section such as a grip section, thereby requiring image transfer means such as image fibers or a lens which has a long optical path. However, the image transfer means such as image fibers or a lens having a long optical path makes a video scope complicated in structure and expensive.

In view of the problems described above, a primary object of the present invention is to provide a video scope which is simple, easy to handle and inexpensive enough for domestic use while requiring no external camera circuit, external power source, external light source or light leading path for illumination.

Apart from the discussion made above, it is emphasized to find and treat decayed teeth in early stages along with a movement to leave 20 teeth at an age of 80 which is promoted by the Ministry of Health and Welfare, etc. Under the current circumstances, babies and children are checked for decayed teeth at health centers and schools, and subjected to treatments after their decayed are pointed out, whereas adult people have small occasions of dental inspection and generally go to dentist's after they feel toothache. In such cases, teeth are badly decayed, thereby requiring many days and high costs for treatments. For checking conditions of teeth at home, it is general to observe the teeth with a single mirror or a combination of such a mirror and a commercially available dental mirror which has a small diameter. However, it is difficult to find decayed teeth at early stages since a single mirror hardly serves for observing sides and rear surfaces of teeth at the back, and even a dental mirror which has a small diameter is ineffective to understand complicated occulusions and cannot provide magnified images. It is therefore demanded to obtain a domestic video scope which is inexpensive and easy to use.

Though a video scope must be strictly sterilized before use, it is not easy to sterilize its portion which comprises an optical mechanism and, it is remarkably difficult from viewpoints of technique and time to completely sterilize even a business video scope which is used by dentists each time an operator shifts to another.

It is much more difficult to sterilize a video scope in a home environment. Even within a family, articles which are used in oral cavities such as tooth brushes are prepared not for common use but for individual use. It is a problem to use a video scope which has not been sterilized even if it has been washed.

Therefore, a cover or the like is fitted over an video signal input section of a video scope. However, people judge a cover as in sanitary from a fear that a thin cover such as a vinyl sack may be broken or that saliva may penetrate through a cover.

When a cover is only fitted over the video signal input section, it is fearful that the cover comes off during use and constitutes a risk of penetration into a throat.

In view of the problems described above, another object of the present invention is to provide a safe video scope which is free from hygienic concerns as injection and accident of dropping of a cover.

SUMMARY OF THE INVENTION

A first video scope according to the present invention is characterized in that it comprises an entry section which can advance into an object, a grip section which is disposed at the back of the entry section so as to be held by an operator: a light reflecting body, an objective lens, a solid-state image pickup device, a light source, a window of incidence for image pickup rays and illumination windows located in the vicinities of the window of incidence being disposed in the entry section, whereas an electric power source for driving at least the light source being disposed in the grip section.

A second video scope according to the present invention is characterized in that an electric circuit for the solid-state image pickup device and a circuit for this solid-state image pickup device are disposed in the grip section of the first video scope.

A third video scope according to the present invention is characterized in that it comprises an entry section which accommodates a light source for emitting rays, a photographing window which allows rays coming from an object to pass therethrough, condenser means which condenses rays emitted from the object and having passed through the photographing window, an image pickup device for converting rays condensed by the condenser means into electric signals and an electric circuit for driving the image pickup device; a grip section which is to be held by an operator of the video scope; and a cover which covers the entry section, and can be fitted and removed over and from the entry section.

A fourth video scope according to the present invention is characterized in that a portion of the cover which corresponds to the photographing window when the cover of the third video scope is fitted over the entry section is made of a substantially transparent resin.

A fifth video scope according to the present invention is characterized in that the electric circuit of third or fourth video scope drives only when the cover is fitted over the entry section.

A sixth video scope according to the present invention is characterized in that fitting operation for the cover of any one of the third through fifth video scope is interlocked with the driving of the electric circuit.

A seventh video scope according to the present invention is characterized in that the cover of a video scope has a discriminating section peculiar to the cover.

DETAILED DESCRIPTION OF THE PREFERRED EMBODIMENTS

Now, the preferred embodiments of the present invention will be described with reference to FIGS. 1 through 17.

First Embodiment

Figure 1:
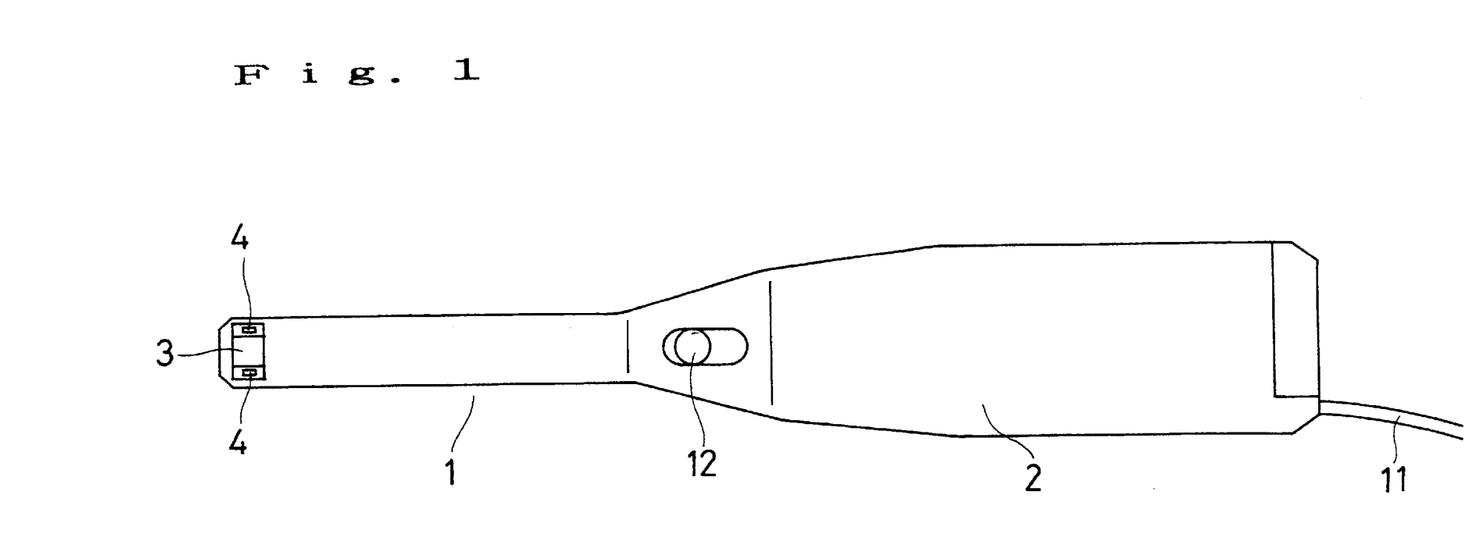
FIG. 1 is an external view of a video scope preferred as a first embodiment of the present invention.
Figure 2:
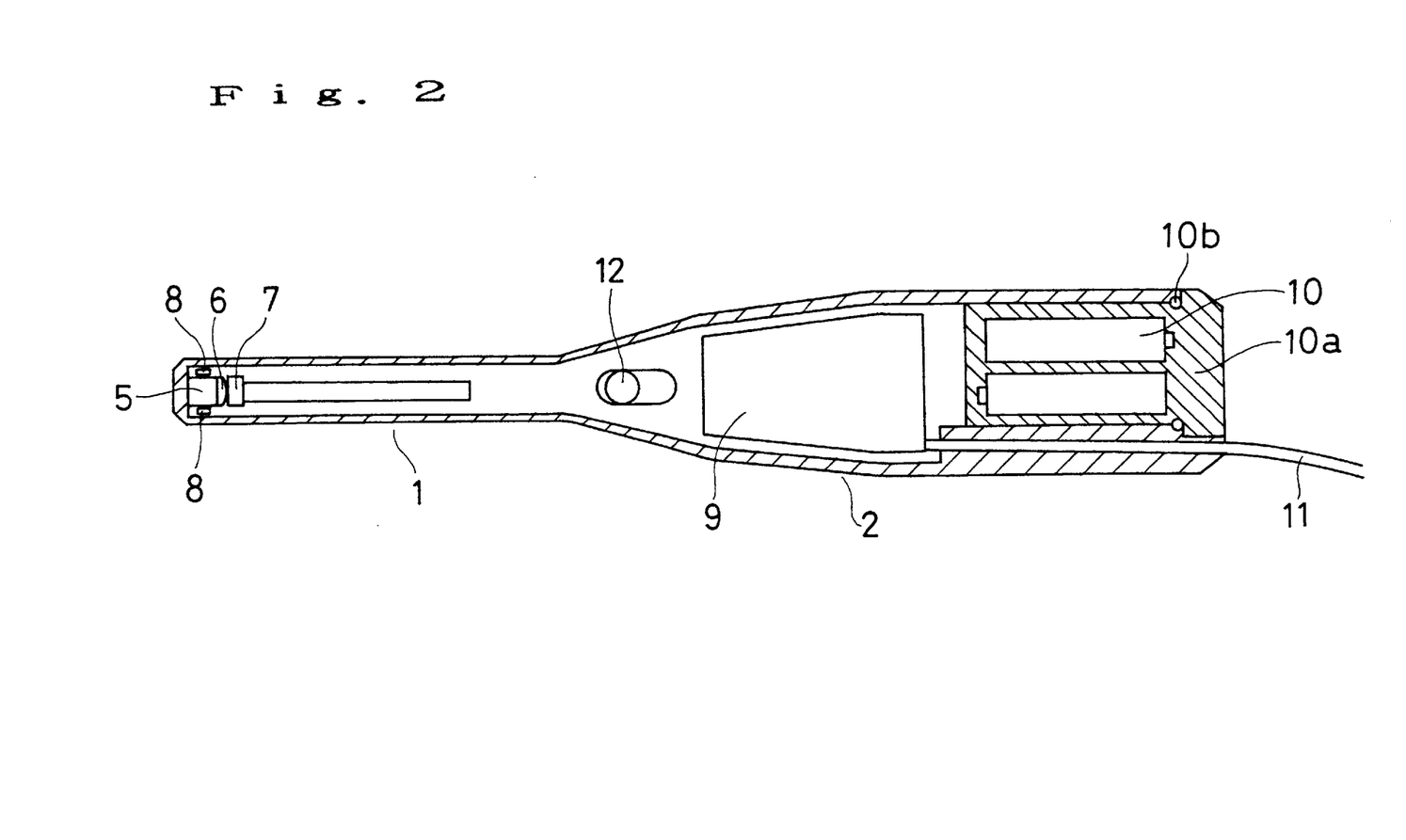
FIG. 2 is a sectional view of the video scope preferred as the first embodiment of the present invention.
Figure 3:
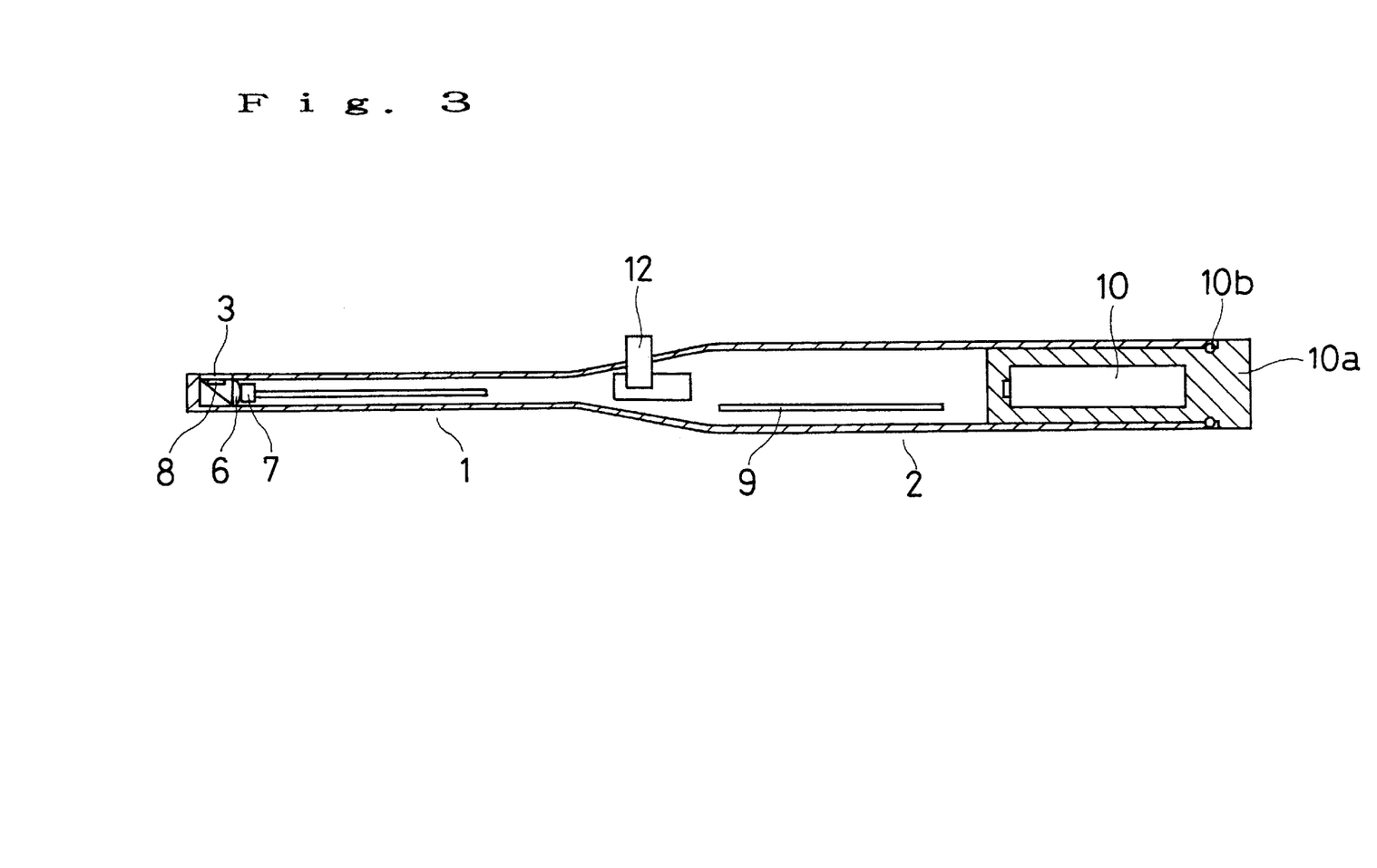
FIG. 3 is a side sectional view of the video scope preferred as the first embodiment of the present invention.
Figure 4:
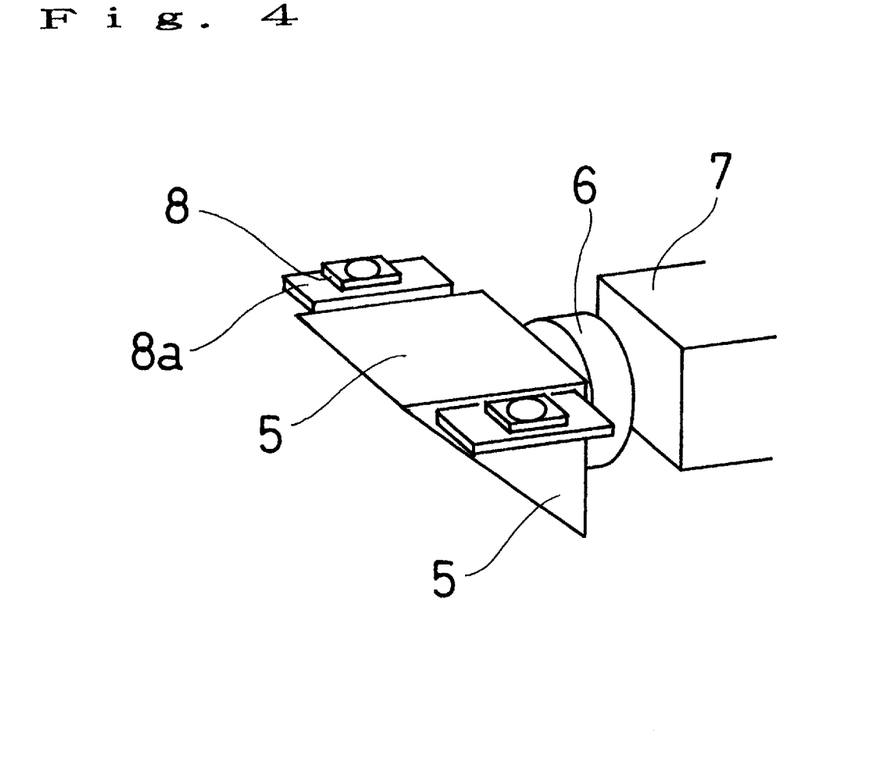
FIG. 4 is a partial enlarged perspective view of the video scope preferred as the first embodiment of the present invention.
Figure 5:
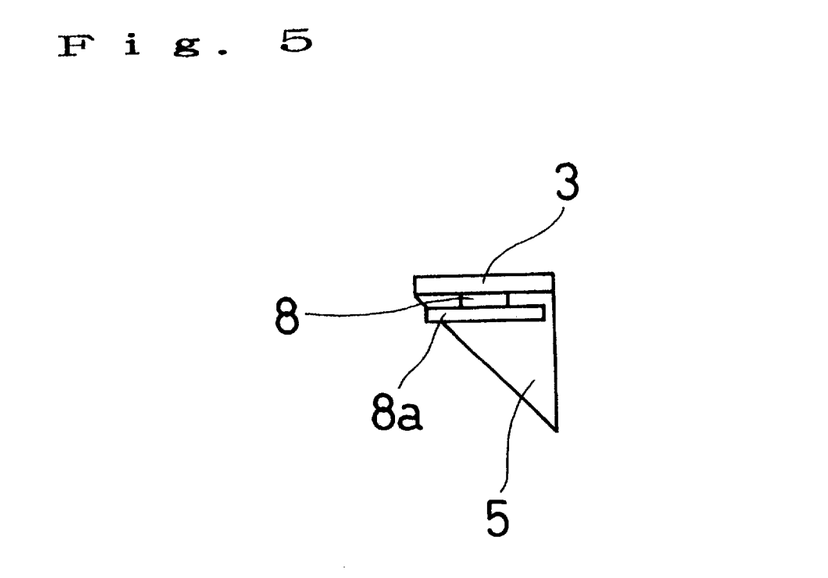
FIG. 5 is a partial enlarged sectional view of the video scope preferred as the first embodiment of the present invention.

FIG. 1 is an external view of a video scope preferred as the first embodiment of the present invention, FIG. 2 is a sectional view of the video scope, FIG. 3 is a side sectional view of the video scope, FIG. 4 is a partial enlarged perspective view and FIG. 5 is a partial enlarged sectional view.

In FIGS. 1 through 5, a reference numeral 1 represents an entry section which is to advance into an oral cavity and a reference numeral 2 designates a grip section which is to be held by a hand of an operator. A window of incidence 3 made of a light transmissive glass material, resin material or the like is hermetically fixed to a side surface of the entry section 1 in the vicinity of a tip thereof, and an image pickup system which consists of a prism mirror 5 used as an example of reflecting body for sideward observation, an objective lens 6 and a CCD unit 7 is built in the tip of the entry section 1. Illumination windows 4 for light projection are disposed on both sides of the window of incidence 3 so that illumination rays emitted from surface mount type white LEDs 8 (Nichia Chemical Industries, Co., Ltd.) mounted on a substrate 8a are projected to the illumination windows 4. The white LEDs 8 are arranged on both sides of the prism mirror 5 and fixed in close contact with the illumination windows 4. Top surfaces of the LEDs 8 are flush with a top surface of the prism mirror 5 as shown in FIG. 5.

The illumination rays are projected directly to the illumination windows 4 so that they are lost at a low ratio and used efficiently. Further, the white LEDs 8 are molded integrally with the illumination windows 4 to reduce a number of required parts and simplify assembling procedures.

Further, the white LEDs 8 are used as a light source so that power consumption is lower than that of lamps. The white LEDs 8 have a long service life and require no exchange with new ones.

An iris diaphragm (not shown) is arranged between the objective lens 6 and the prism mirror 5.

Disposed in the grip section 2 are a camera circuit 9 which operates the CCD unit 7 and the white LEDs 8, and a power source 10 which drives the camera circuit 9 and the white LEDs 8. Built in the camera circuit 9 are a voltage detection circuit which detects a voltage drop in the power source 10 below a predetermined level, a flickering circuit which flickers the white LEDs 8 and a video output interception circuit which turns off a video output. While the power source 10 supplies a voltage at a sufficient level, the white LEDs 8 always stay lit so far as the video output is turned on. When the power source supplies a voltage lower than the predetermined level, however, the voltage detection circuit actuates and flickers the white LEDs 8 and turns off the video signals with the video signal interception circuit.

Usable as the power source 10 are low voltage cells such as alkaline batteries, lithium cells or rechargeable cells. These cells are exchangeably mounted in a power source holder 10a over which a watertight O ring 10b, for example, is fitted and the power source holder 10a is set in the grip section 2. Alternately, a combination of a detachable cell pack and a charger may be used as the power source 10.

A video output cable 11 which is to be connected to a display such as a monitor TV is taken out of a rear portion of the grip section 2. A section of this video output cable which ranges rearward from inside the grip section 2 is made watertight.

A reference numeral 12 represents a switch which is watertightly disposed on the grip section 2 to turn on and off the camera circuit 9. This switch may be used to turn on and off not only the camera circuit 9 but also the white LEDs 8 at the same time, or switchable at three steps: a first step to turn off the camera circuit 9 and the white LEDs 8, a second step to turn on the camera circuit 9, and a third step to turn on the white LEDs 8. Wiring to the power source 10, the camera circuit 9, the CCD unit 7, the white LEDs 8 and the switch 12 will not be described in particular.

The video scope preferred as the first embodiment of the present invention has a simple configuration which consists of an image pickup system, a power source and a light source integrated with one another, and equipped only with video cable, thereby featuring excellent portability.

Further, the video scope preferred as the first embodiment which comprises the voltage detection circuit informs a voltage drop by intercepting the video output while flickering the white LEDs and expresses a trouble in the image pickup system as a condition where no image is formed or an image is disturbed without flickering the white LEDs 8 but keeping them lit, thereby allowing an operator to easily discriminate disturbance of an image due to an insufficient voltage from disturbance of image due to a trouble in the image pickup system itself. to easily know a time for exchanging the power source with a new one and facilitating to handle the video scope. Further, the video scope which allows no disturbed image to be observed prevents a judgment to be made on the basis of an erroneous image in recognition of discoloration caused due to a swollen gum.

Furthermore, the video scope which comprises the image pickup system disposed in the vicinity of the tip of the entry section 1 takes an image of an object directly from the CCD unit, thereby requiring no image transfer means such as relay lenses and lessens degradation in image qualities. Moreover, the video scope is composed watertight as a whole and can easily be washed.

When the video scope is connected to a monitor TV, it permits observing conditions of teeth and gums which can hardly be recognized by eyes, thereby facilitating to check teeth for tartar and decayed conditions.

Figure 6:
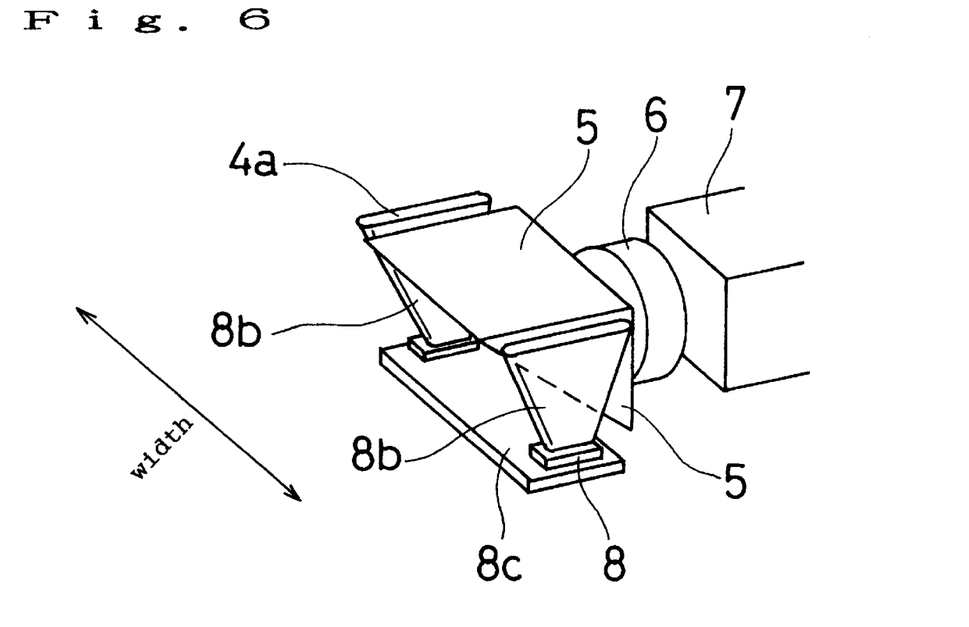
FIG. 6 is a partial enlarged perspective view of a second video scope preferred as the first embodiment of the present invention which is different from that shown in FIG. 4.

FIG. 6 is a partial enlarged perspective view of another embodiment, wherein light leading plates 8b which are made of thin light transmissive glass or transparent resin and have a shape of an inverted trapezoid are fixed in close contact with side surfaces of white LEDs 8, and a substrate 8c is disposed in a space under a slant surface of a prism mirror 5. In this embodiment, upper end surfaces 4a of the light leading plates 8b are kept in close contact with illumination windows 4. When the upper end surfaces are configured to have a thin width, it is possible to allow illumination rays of the same amount to emerge from surfaces which are thinner than those used in the case where the LEDs 8 are kept in close contact with the illumination window 4 as shown in FIG. 4, thereby narrowing the image pickup system, and the entry section thinner and more compact. When the LEDs 8 are to be used in an increased number to enhance luminance, they can be arranged in parallel with each other on a single substrate 8c.

Figure 12:
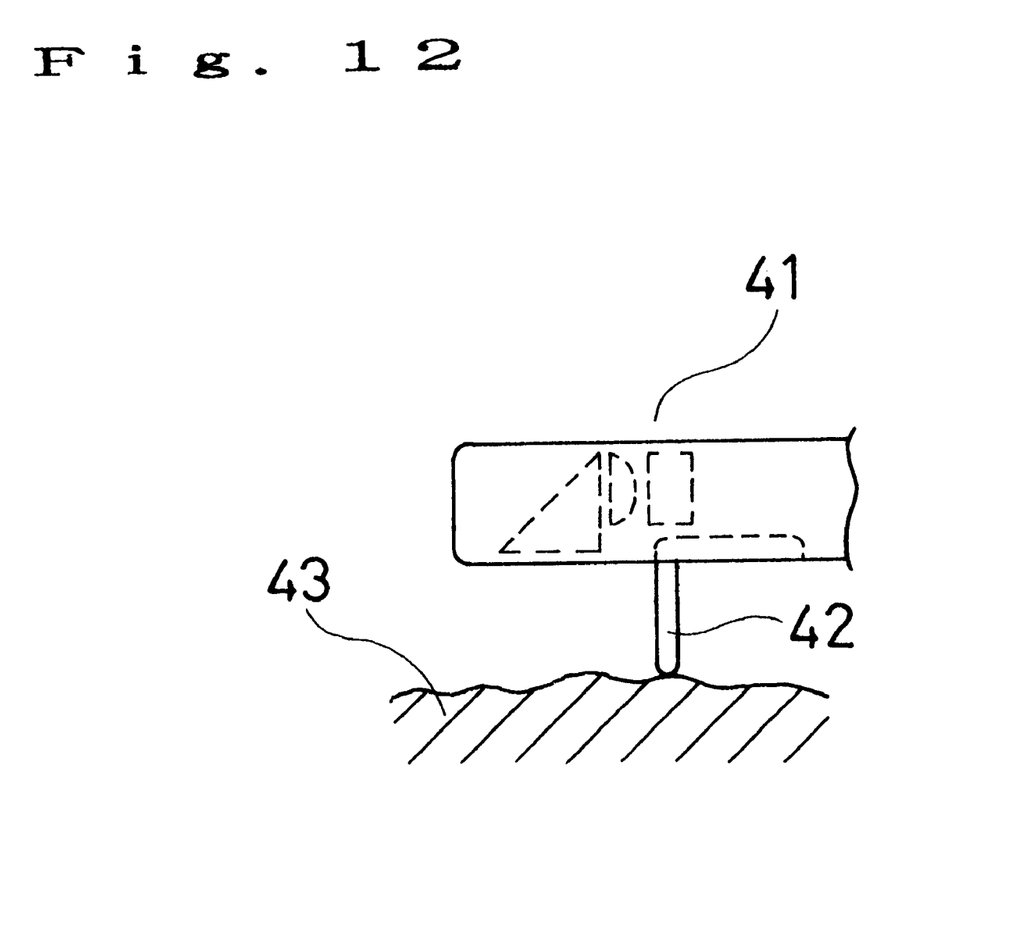
FIG. 12 is a partial side view of the second video scope preferred as the first embodiment of the present invention.

FIG. 12 is a partial side view of a tip of an entry section 41, wherein formed on a surface of incidence of the entry section 41 is a freely foldable rod like positioning member 42 which is accommodated in the entry section 41 in a folded condition and has a length equal to a focal length in a protruding condition. This positioning member 42 may have a plate like shape.

By forming the positioning member 42 and bringing it into contact with an object 43 to be observed, it is possible to hold a video scope always in focus with the object 43 to be observed, thereby reducing manual vibrations and obtaining stable images.

Second Embodiment

Figure 7:
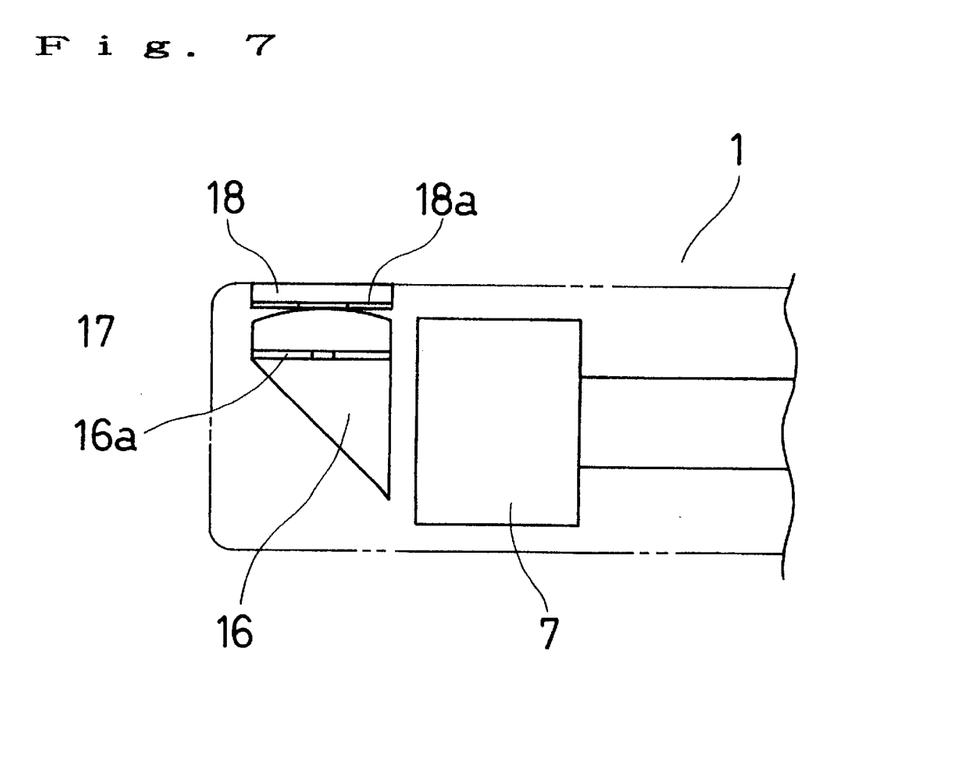
FIG. 7 is a partial enlarged side sectional view of a video scope preferred as a second embodiment of the present invention.

FIG. 7 is a partial sectional view of a tip of an entry section of a video scope, wherein main configuration of a video scope body is similar to that of the first embodiment. A CCD unit 7 and a prism mirror 16 for sideward observation are built in the tip of the entry section 1, and an objective lens 17 is fixed on a side of incidence of the prism mirror 16. A reference numeral 18 represents a window of incidence which is made of glass material, a transparent resin material or the like and hermetically fixed to the entry section 1. A rear stop 16a for the objective lens 17 is integrally formed by printing or the similar technique on a surface of incidence of the prism mirror 16 and a stop 18a is integrally formed by printing or the similar technique on a surface of the window of incidence 18 which is located on a side of the objective lens 17.

A small prism mirror 17 is usable to obtain a required visual field when rays are incident onto the CCD unit 7 directly from the prism mirror 16 as described above though the prism mirror 16 must be large enough not to eclipse a visual field of the objective lens 17 when the objective lens 17 is located before the CCD unit 7 and on the side of incidence of the prism mirror 16.

When a small prism mirror is usable as described above, it is possible to thin the entry section 1 by using a small prism mirror, and reduce a number of required parts for reduction of a manufacturing cost of a video scope by forming a stop integrally by printing or the similar technique.

Third Embodiment

Figure 8:
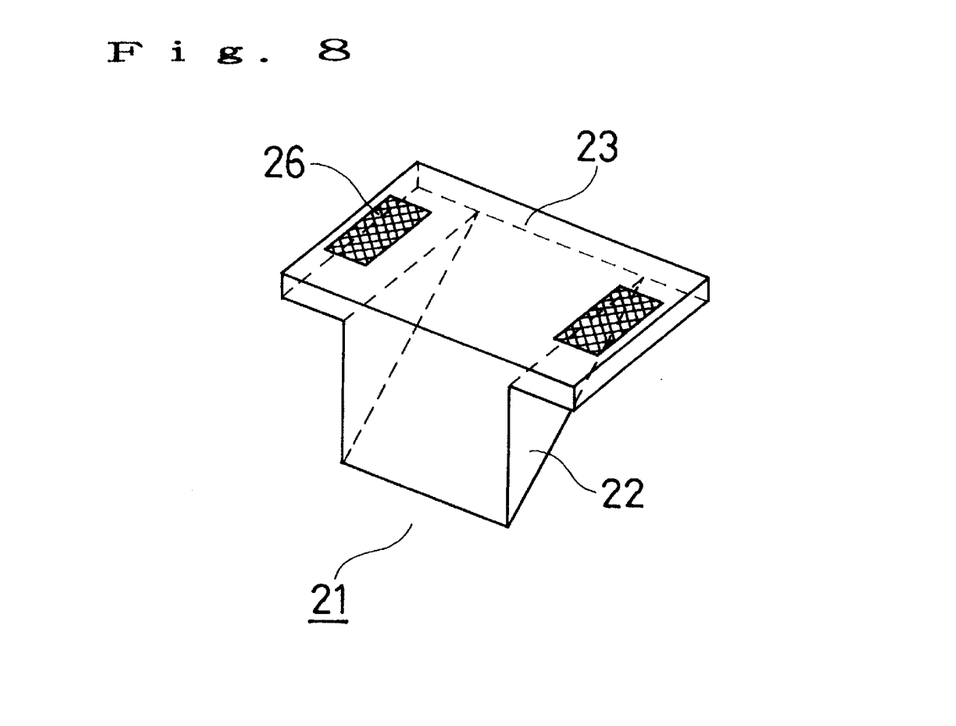
FIG. 8 is a partial perspective view of a video scope preferred as a third embodiment of the present invention.
Figure 9:
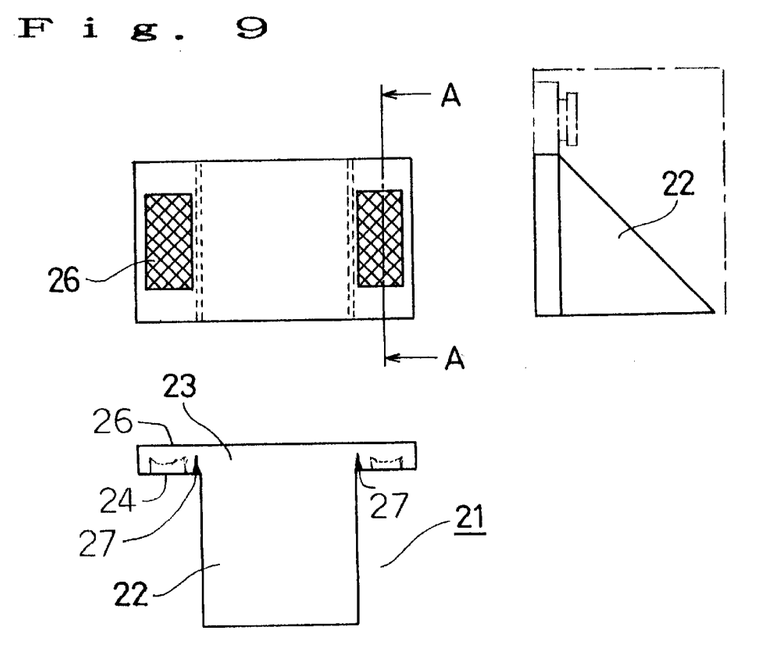
FIG. 9 is a partial view of three surfaces of the video scope preferred as the third embodiment of the present invention.
Figure 10:
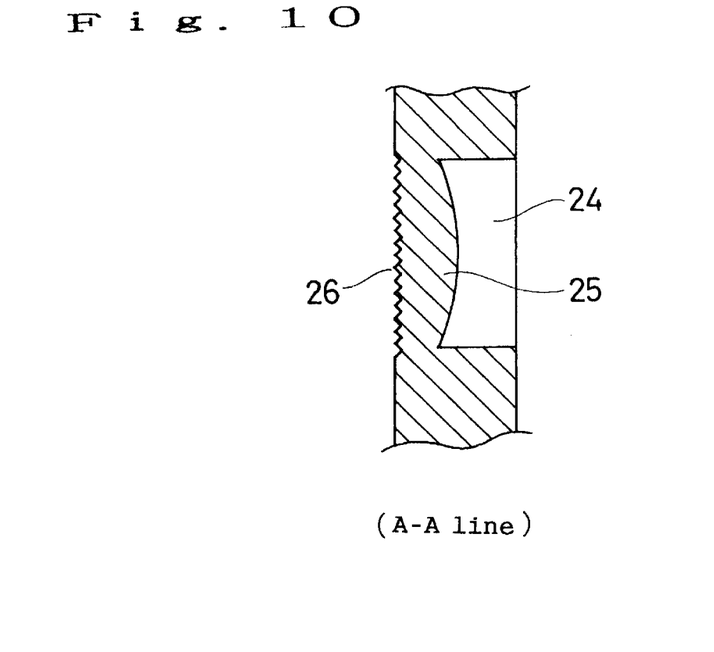
FIG. 10 is a partial enlarged sectional view of the video scope preferred as the third embodiment of the present invention.

FIG. 8 is a perspective view of an imaging optical part 21, FIG. 9 is a view illustrating three surfaces of the imaging optical part 21 and FIG. 10 is a partial enlarged sectional view of the imaging optical part 21 taken along an A—A line. In FIGS. 8 through 10, a reference numeral 21 represents the imaging optical part to be used in an entry section of a video scope. This video scope has a body having a main configuration which is similar to that of the first embodiment. The imaging optical part 21 consists of a prism mirror section 22 and a window of incidence 23 which are formed as an integral molding of a transparent resin such as transparent acrylic resin which is a light transmissive material. Illumination windows 24 for light projection are disposed on both sides respectively of the window of incidence 23 and white LEDs are fixed under the illumination windows 24. A side of incidence of the illumination window 24 is formed in a shape of a lens 25 which condenses illumination rays coming from the white LEDs, whereas a light dispersing surface, for example, a diffraction grating 26 for light dispersion is formed on a side of emergence.

An illumination range can be broadened and uniform illumination can be performed by forming the diffraction grating 26 for light dispersion, and illumination rays can be utilized with a higher efficiency by condensing the illumination rays coming from the white LEDs with the form of lens 25. Dependently on locations of the white LEDs, a small portion of rays emerging from the white LED may be reflected by the window of incidence 23, etc. and enter the prism mirror section 22, thereby producing the so-called flare phenomenon on a surface of an image. However, it is possible to prevent leaking rays from entering the prism mirror section 22 by forming notches between the illumination windows 24 and the prism mirror section 22, and integrally burying light shielding parts 27 as shown in FIG. 9.

The white LEDs may be located not on a side surface of the prism mirror 22, but on a slant surface of the prism mirror 22, or on a tip of an entry section, as indicated by a chain line in FIG. 9 so that rays are projected therefrom.

Figure 11:
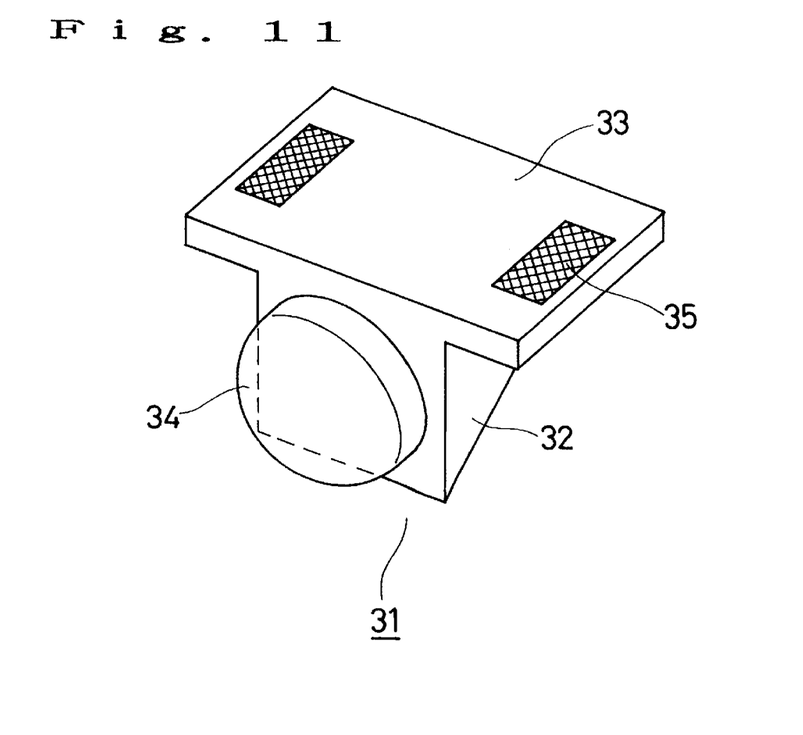
FIG. 11 is a partial perspective view of the video scope preferred as the third embodiment of the present invention.

In FIG. 11, a reference numeral 31 represents an imaging optical part formed as an integral molding which is made of a transparent resin such as a transparent acrylic resin which is a light transmissive material, and consists of a prism mirror section 32, a window of incidence 33 and an objective lens section 34. Illumination windows for light projection are disposed in the window of incidence 33, white LEDs are fixed to these illumination windows like those described above, a condenser lens is formed on a side of incidence of illumination rays as shown in FIG. 10 and diffraction gratings 35 for dispersing rays are formed on a side of emergence.

These imaging optical parts 21 and 31 make it possible to reduce a number of required parts, simplify assembling procedures, and moreover lessen a weight of a video scope and lower a manufacturing cost thereof since they are formed as an integral molding of resin.

Fourth Embodiment

Figure 13:
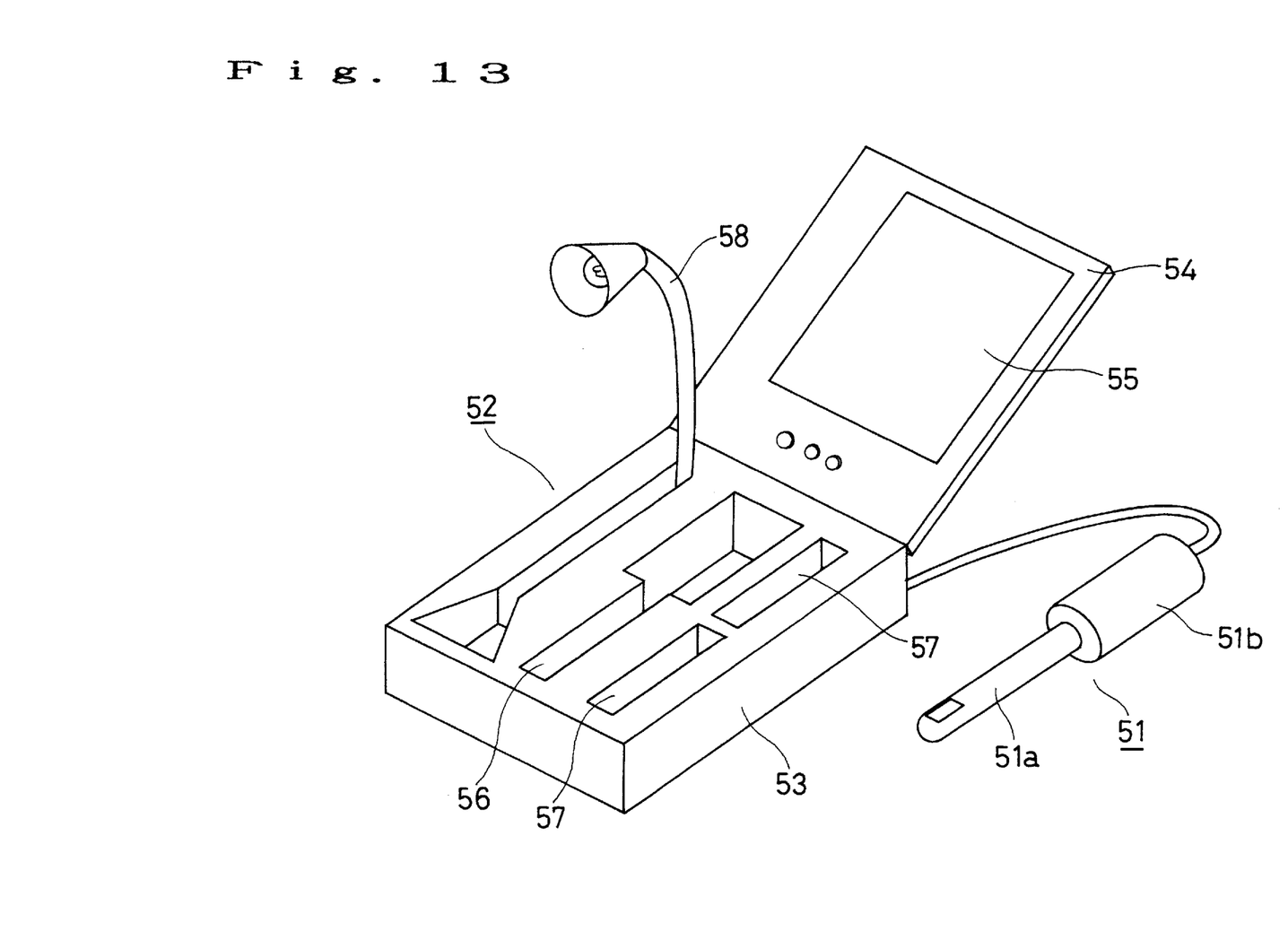
FIG. 13 is an external view of a video scope which is accommodated in a case with a display preferred as a fourth embodiment of the present invention.

FIG. 13 is an external view of a portable case which is equipped with a display and a video scope. A reference numeral 51 represents a video scope comprising an image pickup system consisting of a solid-state image pickup device, a lens and a prism mirror for sideward observation which are disposed in a tip of an entry section 51a, and a circuit for the solid-state image pickup and a power source disposed in a grip section 51b. A reference numeral 52 designates a portable case with a display consisting of a body 53 and a lid 54 which is hinged by a side of the body 53 so that it can open and close while freely rotating, and can stop at an optional position. This lid 54 comprises a display unit 55 which uses a thin display such as a liquid crystal cell. Disposed in the body 53 are an accommodator 56 for accommodating the video scope 51, an equipment accommodator 57 for accommodating exchange covers, optical adapters (not shown) for observing ear holes and skins, etc., an illumination stand 58 which can be freely folded, elongated and contracted, and a mirror (not shown).

The display unit 55 and the illumination stand 58 are driven by a battery or an AC power source (not shown) which is connected thereto. The video scope 51 is connected to the display unit 55 directly or by way of a terminal which is connectable also to a separate monitor TV.

The illumination stand 58 is usable as an auxiliary illumination lamp for illuminating an oral cavity when the video scope is used in a dark environment.

The mirror which is fixed to the body 53 is usable for observing a face as a whole, and recognizing a portion whose image is to be picked up and an oral cavity as a whole. This mirror may be fixed to the lid 54 and a surface of the display unit 55 may be formed as a half mirror so that it has a function of an ordinary mirror.

As understood from the above, when the video scope 51 is accommodated in the portable case with the display unit 55, the video scope can easily be carried and used conveniently at a location where no monitor TV is available or in an outdoor environment.

Fifth Embodiment

Figure 14:
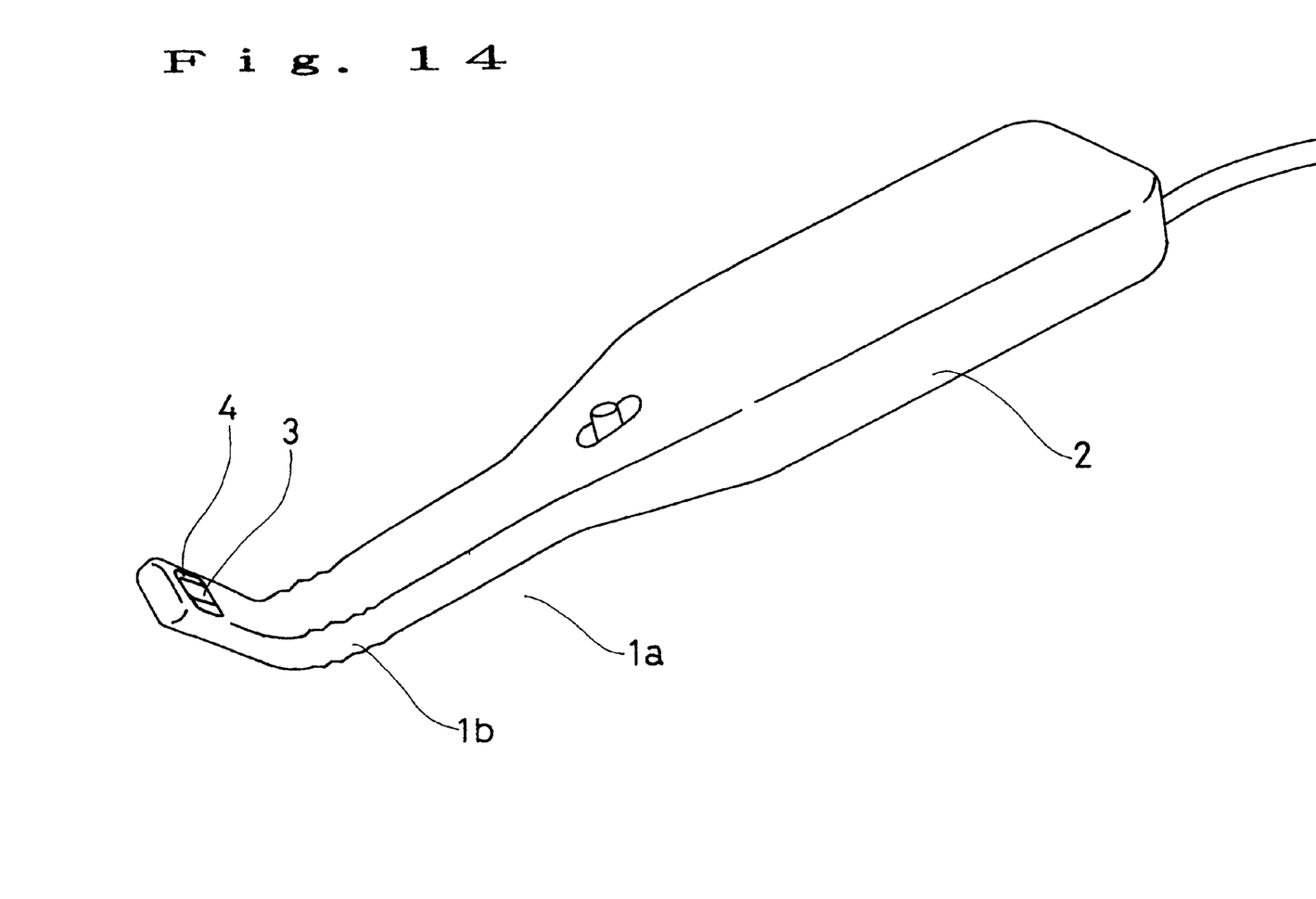
FIG. 14 is a partial perspective view of a video scope preferred as a fifth embodiment of the present invention.

FIG. 14 is a perspective view of a video scope preferred as a fifth embodiment of the present invention. This video scope has a body which has a main configuration similar to that of the first embodiment. Speaking concretely, the video scope comprises an image pickup system consisting of a CCD unit, a lens and a prism mirror for sideward observation in addition to white LEDs which are disposed in tip of an entry section 1a, has an incidence window 3 and illumination windows 4, and a camera circuit and a power source disposed in a grip section 2.

A flexible portion 1b which can be bent and fixed at an optional angle is formed as a portion, for example a middle portion or nearby, of the entry section 1a. This flexible portion 1b may be located within a range from the middle portion to the grip section 2 or around a border between the entry section 1a and the grip section 2. The flexible portion 1b may be, for example, a bellows like bendable portion, a flexible tube covered with a rubber sheath or a combination of spiral tubes so far as it can be bent, fixed at an optional angle and handled freely.

The video scope can be fixed at an optional angle by bending the flexible portion 1b of the entry section 1a, The flexible portion 1b may be bent by hand or with a tool such as a lever.

The video scope which has the flexible section 1b does not oblige an operator to take an unnatural attitude for holding the video scope, lessens fatigue of his hands or facilitates to handle the video scope and is usable to observe a location which cannot be observed straightly.

Sixth Embodiment

Figure 15:
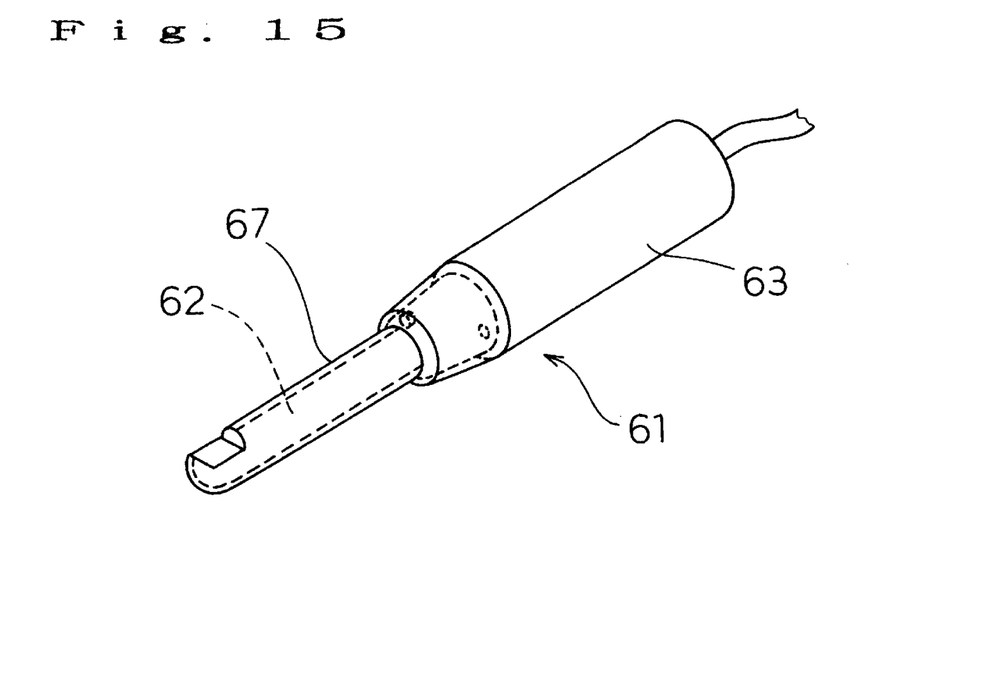
FIG. 15 is an external view of a video scope preferred as a sixth embodiment of the present invention.
Figure 16:
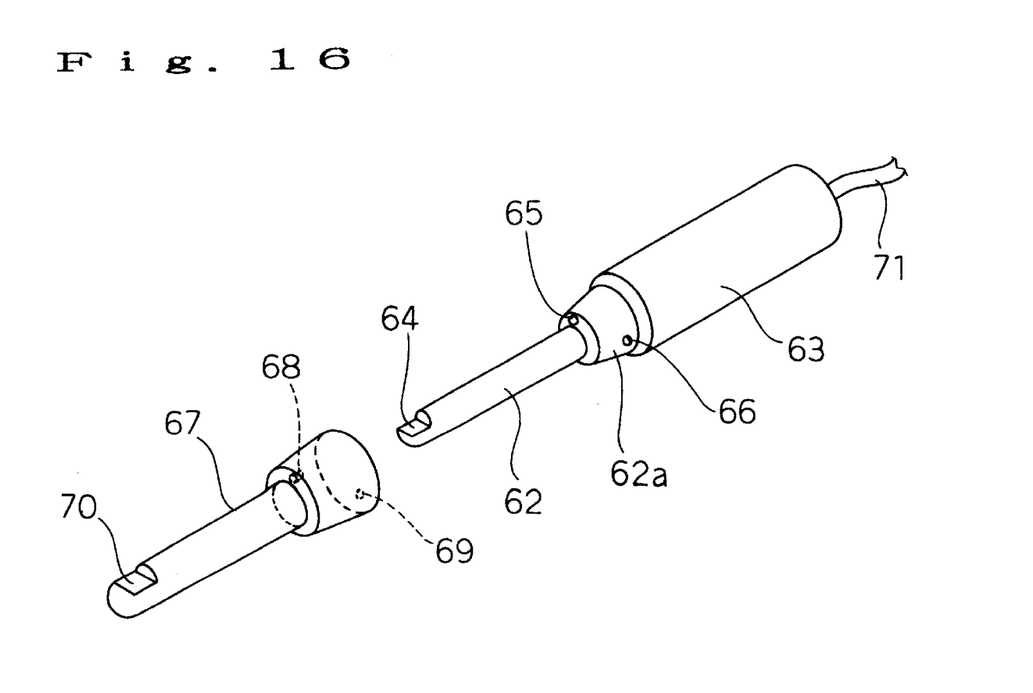
FIG. 16 is an external view illustrating the video scope preferred as the sixth embodiment of the present invention in a condition where a cover is removed.
Figure 17:
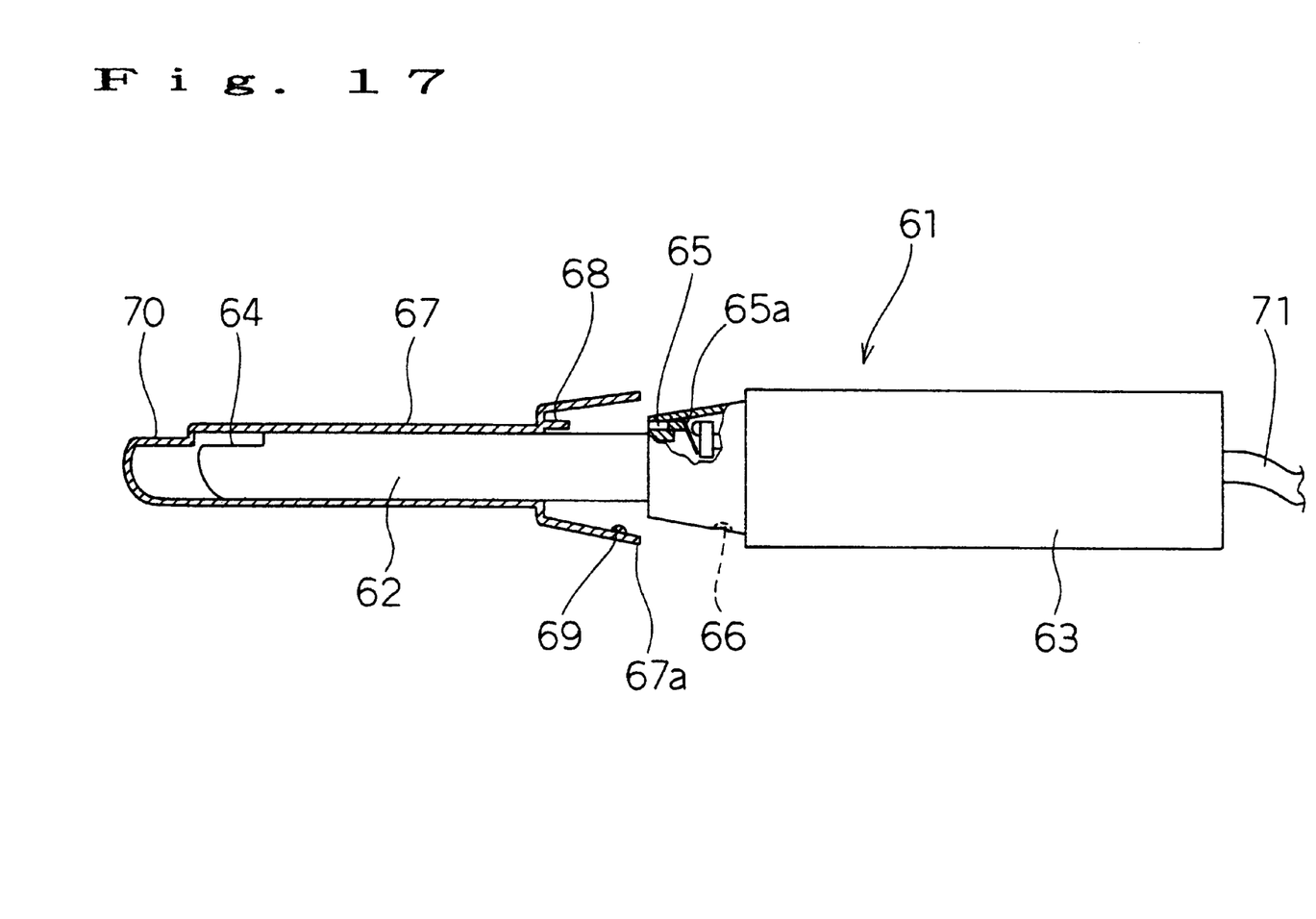
FIG. 17 is a side view including a partial sectional view of the video scope preferred as the sixth embodiment of the present invention.

FIG. 15 is an external view of a video scope preferred as the sixth embodiment of the present invention, FIG. 16 is an external view illustrating the video on a condition where a cover is removed from the video scope and FIG. 17 is a side view including a partial sectional view of the video scope.

In FIGS. 15 through 17, a reference numeral 61 represents a video scope consisting of an entry section 62 which is to be advanced into an oral cavity by an operator of the video scope and a grip section 63 which is to be held by a hand of the operator. A photographing window 64 made of a light transmissive glass material or a transparent resin is hermetically fixed to a side surface in the vicinity of a tip of the entry section 62, and an image pickup system (not shown) which consists of a prism mirror for sideward observation, an objective lens, an iris diaphragm and a CCD unit is built in the entry section 62. The CCD unit may be built in the grip section 63 and an image may be transferred from the entry section 62 through image guide fibers. Further, illumination rays which are emitted from white LEDs disposed in the vicinities of the tip are projected through the photographing window 64.

Disposed in the grip section 93 are a camera circuit (not shown) for operating the CCD unit, and a power source for driving the camera circuit and the white LEDs. Usable as the power source are low voltage cells such as alkaline batteries, lithium cells, rechargeable cell or a combination of a detachable cell pack and a charger. A control button (not shown) for turning on and off the camera circuit is disposed on the grip section 63 and a video output cable 71 which is to be connected to a display unit such as a TV is taken out of a rear surface of the video scope.

A tapered rear entry section 62a is disposed at the back of the entry section 62, or on a side of the grip section 63, and a step is formed between the entry section 62 and the rear entry section 62a. An opening 65 for switch is watertightly formed in an end surface of the step between the entry section 62 and the rear entry section 62a, and a switch 65a for turning on the power source is disposed in a depth of this opening 65. Further, a fixing cavity 66 or a plurality of fixing cavities 66 are formed in the tapered surface of the rear entry section 62a.

A reference numeral 67 represents a cover which covers the entry section 62 and the rear entry section 62a. The cover 67 is entirely made of a transparent resin or only a tip window portion 70 which corresponds to the photographing window 64 when the cover is fitted on the grip section 63 is made of the transparent resin and the rest portion is made of a colored resin so that the cover is washable. The tip window portion 70 has a planar surface at a location which corresponds to the photographing window 64 of the entry section 62. A protrusion 68 for depressing the switch 65a and a fixing protrusion 69 or a plurality of fixing protrusions 69 are integrally formed in a tapered opening 67a of the cover 67.

When the operator fits the cover 67 over the entry section 62 while adequately turning the cover 67 so that the tip window portion 70 corresponds to the photographing window 64 of the entry section 62, the protrusion 68 for switch formed in the tapered opening 67a is inserted into the opening 65 for switch formed in the rear entry section 62a. When the cover 67 is further fitted, the protrusion 68 for switch depresses the switch 65a in the opening 65, thereby turning on the power source of the video scope 61. When the power source of the video scope 61 is turned on, the video scope can be driven with the control button, and the camera circuit and the white LEDs are operated by turning on the control button. When the power source of the video scope 61 is turned on, the fixing protrusion 69 of the cover 67 is inserted fits into the fixing cavity 66 of the rear entry section 62a, thereby fixing the cover 67.

When the control button is turned on in this condition, an image is formed on a display unit such as a TV to which the video output cable 71 is connected.

As for a configuration to activate the switch, electric terminals may be disposed at locations on the cover 67 and the entry section 62 which are to be brought into contact with each other so that the video scope can be electrically energized when the cover 67 is fitted. Such a configuration will not be described in details since various configurations are conceivable by combining the known techniques. To fit and fix the cover 67, it is possible, for example, to adopt a configuration of a tapping formed in the vicinity of the opening of the cover 67 and a ring screw disposed on the grip section 63 so that the cover can be screwed and fixed over the ring screw, the switch is turned on by turning the ring screw and the power source is turned on by fitting the cover. Further, the entry section 62 may have a form which is not cylindrical and the photographing window 64 may be located not on the side surface but on the tip of the entry section 62.

That is, the video scope is configured so that the power source is turned on (set in an electrically energized condition) or becomes usable by fitting and fixing the cover 67, or a voltage is not supplied, the camera circuit and the power source are not operated even by manipulating the control button, and the video scope is unusable so far as the cover 67 is correctly fitted and fixed. Further, it is possible to omit the control button, and configure the video scope so that the power source and the camera circuit are driven simply by fitting and fixing the cover 67.

Since the power source or the power source and the camera circuit cannot operate so far as the cover 67 is not fitted, the video scope cannot be used in an insanitary condition or without the cover 67. Further, the video scope prevents accidents such as swallowing of the cover which comes off during use, or suffocation since the cover is different from a vinyl sack or a cover which is fitted simply and loosely.

When a color line is traced on the cover 67 or it is colored as described above, it can easily be recognized so that each person can use a cover which is prepared for his exclusive use and is free from a fear of insanitation such as infection.

The video scope 61 may be used as a part of a magnifier for display on a TV. In such a case, the cover 67 may be used in a specific field, for example, observation of skins, head skins or insects.

Mass production of the cover 67 which is made of a resin will serve for lowering of a manufacturing cost thereof and making the cover disposable.

As understood from the foregoing description, the present invention makes it possible to obtain an inexpensive video scope which eliminates the necessity to use expensive parts such as relay lenses and parts of optical fibers having complicated forms, allows power consumption to be lowered by using white LEDs, permits simplifying assembling procedures and lowering a manufacturing cost by utilizing simple dry element cells, facilitates handling by flicking a power source to inform a time for exchanging the dry element cells and is apt to prevail for domestic use.

As apparent from the foregoing description, the invention is capable of providing a video scope which eliminates a fear of insanitation by fitting a cover over an entry section of the video scope and substantially completely prevents the cover from coming off.

Further, the video scope according to the present invention a cover to be fitted by an operator before use since it is configured so that fitting of the cover is a factor indispensable for turning on a power source, or so that the video scope does not operate so far as the cover is fitted and fixed correctly. Accordingly, this video scope gives a feeling of hygienic safety.

What is claimed is:

1. A video scope comprising:

an entry section which advances into an object; and a grip section which is disposed rearwardly of said entry section for holding by an operator;

said entry section including a light reflecting body, an objective lens, a solid-state image pickup device, a light source, a window of incidence for image pickup rays and illumination windows located in the vicinities of the window of incidence; and said light source and said illumination windows formed as an integral molded piece.

2. A video scope according to claim 1, wherein said solid-state image pickup device, said objective lens, said light reflecting body and said window of incidence are arranged in this order.

3. A video scope according to claim 2, wherein said reflecting body, said window of incidence and said illumination windows are made of a transparent resin which is a light transmissive material and integrally formed.

4. A video scope according to claim 1, wherein said solid-state image pickup device, said light reflecting body, said objective lens and said window of incidence are arranged in this order.

5. A video scope according to claim 1, wherein said light source is composed of white LEDs.

6. A video scope according to claim 2,
wherein said light source is composed of white LEDs.

7. A video scope according to claim 3,
wherein said light source is composed of white LEDs.

8. A video scope according to claim 1,
wherein said light source is disposed under a reflecting surface of said reflecting body and
wherein light leading members which lead illumination rays to said illumination windows are disposed between said illumination windows and said light source, and beside said reflecting surface.

9. A video scope according to claim 1,
wherein condenser lenses which condense said illumination rays are formed integrally with surfaces of incidence of said illumination windows and dispersion surfaces for dispersing rays are formed integrally with surfaces of emergence of said illumination windows.

10. A video scope according to claim 1,
wherein a foldable focal point positioning member is disposed on a surface of incidence of said entry section.

11. A video scope according to claim 1 further comprising:
a voltage detection circuit which detects a voltage drop in said power source;
and a flickering circuit which flickers said light source,
wherein said flickering circuit operates on the basis of a detection output from said detection circuit.

12. A video scope according to claim 1 further comprising:
a voltage detection circuit which detects a voltage drop in said power source; and
a video output variation circuit which varies a video output from said solid-state image pickup device on the basis of a detection output from said detection circuit.

13. A video scope according to claim 1,
wherein a flexible portion which is capable of maintaining an optional bent condition is formed in said entry section.

14. A video scope comprising:
an entry section which advances into an object; and
a grip section which is disposed rearwardly of said entry section for holding by an operator;
said entry section including a light reflecting body, an objective lens, a solid-state image pickup device, a light source, a window of incidence for image pickup rays and illumination windows located in the vicinities of the window of incidence;
wherein at least a power source is disposed in said grip section for driving said light source,
said light source is disposed under a reflecting surface of said reflecting body, and
light leading members which lead illumination rays to said illumination windows are disposed between said illumination windows and said light source, and beside said reflecting surface.

15. A video scope comprising:
an entry section which advances into an object; and
a grip section which is disposed rearwardly of said entry section for holding by an operator;
said entry section including a light reflecting body, an objective lens, a solid-state image pickup device, a light source, a window of incidence for image pickup rays and illumination windows located in the vicinities of the window of incidence;
wherein at least a power source is disposed in said grip section for driving said light source,
said solid-state image pickup device, said objective lens, said light reflecting body and said window of incidence are arranged in the aforementioned order, and
said reflecting body, said window of incidence and said illumination windows are made of a transparent resin which is a light transmissive material and is integrally formed.

16. A video scope comprising:
an entry section which advances into an object; and
a grip section which is disposed rearwardly of said entry section for holding by an operator;
said entry section including a light reflecting body, an objective lens, a solid-state image pickup device, a light source, a window of incidence for image pickup rays and illumination windows located in the vicinities of the window of incidence;
wherein at least a power source is disposed in said grip section for driving said light source, and
a foldable focal point positioning member is disposed on a surface of incidence of said entry section.

17. A video scope comprising:
an entry section which advances into an object; and
a grip section which is disposed rearwardly of said entry section for holding by an operator;
said entry section including a light reflecting body, an objective lens, a solid-state image pickup device, a light source, a window of incidence for image pickup rays and illumination windows located in the vicinities of the window of incidence;
wherein at least a power source is disposed in said grip section for driving said light source,
a voltage detection circuit detects a voltage drop in said power source; and
a flickering circuit flickers said light source and operates in response to a detection output from said detection circuit.

18. A video scope having an entry section for insertion into an object, comprising
a light source,
a window for permitting said light to exit from said entry section and re-enter after being reflected off said object,
an objective lens,
a solid state image pickup device coupled to said objective lens for converting said light into a video signal, and
a prism disposed between said window and said objective lens for directing said light to said image pickup device,
said light source, window, objective lens, and solid state pickup device are disposed within said entry section,
a power source for energizing said light source and image pickup device,
a detection circuit for detecting a voltage drop in said power source, and
a flickering circuit connected between said detection circuit and said light source for flickering said light source when a voltage drop is detected.

* * * * *